United States Patent [19]

Miller

[11] 4,045,725
[45] Aug. 30, 1977

[54] ROTATING ASYMMETRIC ELECTRODE FOR MEASURING CHARACTERISTICS OF ELECTROCHEMICAL CELLS

[75] Inventor: Barry Miller, Murray Hill, N.J.

[73] Assignee: Bell Telephone Laboratories, Incorporated, Murray Hill, N.J.

[21] Appl. No.: 665,091

[22] Filed: Mar. 8, 1976

[51] Int. Cl.² .......................................... G01N 27/42
[52] U.S. Cl. ................... 324/30 B; 324/29; 324/65 R; 324/118; 204/199
[58] Field of Search ............. 324/29, 65 R, 30 R, 324/30 A, 30 B, 118; 204/199, 200, 201, 220

[56] References Cited

U.S. PATENT DOCUMENTS

| | | | |
|---|---|---|---|
| 2,344,859 | 3/1944 | Fox | 324/30 R |
| 2,458,676 | 1/1949 | Brenner et al. | 204/199 |
| 3,365,376 | 1/1968 | Weyland | 324/29 |
| 3,385,774 | 5/1968 | Thompson et al. | 204/199 |
| 3,924,175 | 12/1975 | Wilson | 324/30 R |

Primary Examiner—Rudolph V. Rolinec
Assistant Examiner—Michael J. Tokar
Attorney, Agent, or Firm—George S. Indig

[57] ABSTRACT

In an electrochemical cell passing a constant current, an electrode rotating asymmetrically with respect to a fixed electrode produces an ac voltage, having a component at the rotational frequency, between the rotating and fixed electrodes because the interelectrode distance and dc solution resistance between the electrodes vary. When this electrode is used in an operating two electrode cell, e.g., a plating bath, the ac voltage may be used to map the spatial current distribution. Measurements of solution conductivity may also be made.

7 Claims, 6 Drawing Figures

ROTATING ASYMMETRIC ELECTRODE FOR MEASURING CHARACTERISTICS OF ELECTROCHEMICAL CELLS

BACKGROUND OF THE INVENTION

1. Field of the Invention

This invention relates generally to electrochemical cells and more particularly to the measurement of characteristics, such as solution conductivity and spatial current distribution, of operating electrochemical cells.

2. Description of the Prior Art

Solution conductivity measurements in electrochemical cells are typically made by ac bridge techniques because of the problems involved in overcoming electrode polarization when dc techniques are used. Although dc techniques have been developed that overcome these problems, most require a constant open circuit potential and non-polarizable reference type electrodes which raise possibilities of incompatibility with or contamination of the cell solution. Avoidance of electrode polarization by using a small current results in an IR drop that is too small to be easily measured without cumbersome apparatus that is not well adapted to routine use.

Measurement of spatial current distribution in operating electrochemical cells depends upon the measurement of the voltage between two electrodes. However, the measured voltage depends upon the alignment of the electrodes with respect to the current direction and can vary from a maximum value when the line connecting the probes is parallel to the current direction to zero when the line between the probes is perpendicular to the current direction. Some uncertainty is thus introduced into the measured voltage which makes rapid and precise measurements difficult.

SUMMARY OF THE INVENTION

An electrode moving asymmetrically with respect to a fixed electrode can be used to measure characteristics, such as cell conductivity or spatial current distribution, of operating electrochemical cells. Because of the asymmetry, the distance and dc solution resistance between the moving electrode and a fixed cell electrode vary. If the moving electrode rotates asymmetrically with respect to a fixed electrode at a constant angular velocity and a constant current passes through the cell, the voltage drop between the moving electrode and the fixed cell electrode varies periodically because of the periodic variation in the resistance between the asymmetrically rotating electrode and the cell electrode. DC solution conductivity is measured without reference type electrodes or cumbersome apparatus. If the asymmetrically rotating electrode is used with a working two electrode electrochemical cell, the spatial current distribution is easily determined without any inaccuracies from variations in the voltage measured arising from the particular alignment of the electrodes with respect to the direction of current flow as the voltages for all alignments of the rotating electrode with respect to the direction of current flow, i.e., from parallel to perpendicular, are measured.

DETAILED DESCRIPTION

Figure 1:
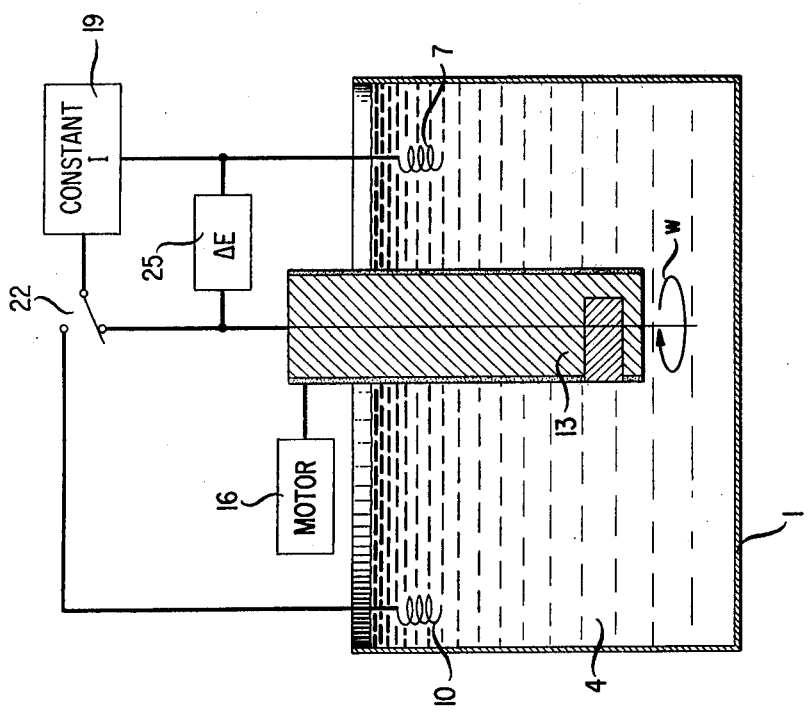
FIG. 1 is a partially sectional and partially schematic view of apparatus used with this invention.

Apparatus for use with this invention is shown in outline in FIG. 1. Within electrochemical cell 1, which is filled with an electrolytic solution 4, are two conventional electrodes 7 and 10. Moving electrode 13 is positioned within cell 1 and suitably supported by means that are not shown. A motor and associated control circuitry 16 provide means for moving electrode 13 about a vertical axis at an angular velocity $\omega$ which may or may not be variable. Typical rotational velocities are between 400 and 6,000 revolutions per minute. A constant current source 19 is connected to electrode 7 and through switch 22 to either electrode 10 or electrode 13 and provides means for passing a constant current through cell 1. Cell 1 may thus be operated in either a two or three electrode mode, or if so desired, switch 22 may be omitted and the current source connected so that the electrochemical cell operates permanently in either a two or three electrode version. Voltage measuring apparatus 25 provides means for measuring the voltage between electrodes 7 and 13.

It has been found that solution conductivity measurements and spatial current distribution mapping are easily made if moving electrode 13 has a geometry and is moved to periodically vary the distance between it and electrode 7. As the interelectrode distance varies, the resistance between electrodes 7 and 13 varies and because of the constant current through the cell, the voltage between electrodes 7 and 13 has an ac component that also varies periodically. Analysis of the ac voltage permits determination of solution conductivity or spatial current distribution. Many geometries and means for moving electrode 13 that vary the dc solution resistance between the electrodes are possible and included within the scope of this invention although only several will be described.

Figure 2B:
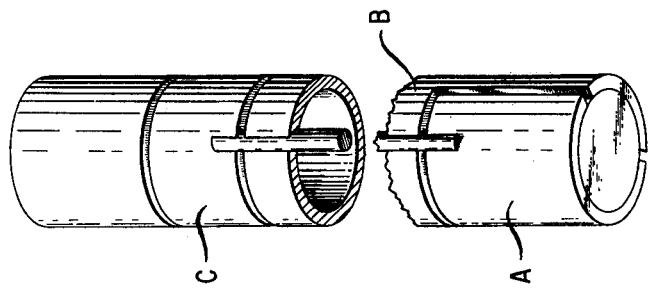
FIGS. 2A and 2B are a cross-sectional and perspective view, respectively, of two embodiments of the rotating electrode.
Figure 2A:
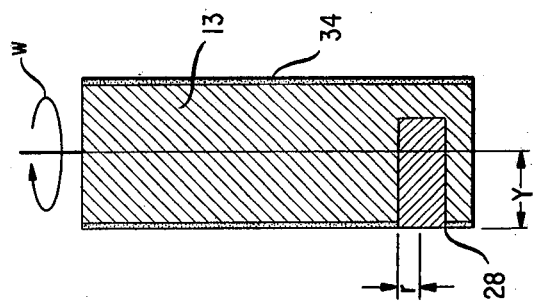

Although electrode 13 can move in any manner varying the distance between it and the fixed electrode including rectilinearly, all such movement might not be perpendicular to the equipotential lines and would not measure the maximum possible voltage for a given linear movement. Assurance that the maximum voltage is measured in a given plane of rotation is possible by rotating the electrode 360°. The electrode configurations shown in FIGS. 2A and 2B are suitable for such rotation and will be described in some detail. The electrodes are asymmetric with respect to the indicated axes of rotation and electrode rotation varies the solution resistance between the moving and fixed electrode. Symmetric electrodes, e.g., a ring, are included within the invention when rotated about an axis displaced from the center of the ring. The axis of rotation of the electrode need not be perpendicular to the plane of the ring or of any other two dimensional electrodes. Such off-axis rotation produces a variation in the distance and resistance between the rotating and the fixed electrode.

The configuration shown in FIG. 2A is rotating disc electrode 13 with a disc 28 having a radius $r$ and spaced a distance $y$ from the axis of rotation. Disc 28 is oriented so that the plane of disc 28 is parallel to the axis of rotation and is spaced within the solution a distance from electrode 7 that is much greater than $r$. An extended discussion of Laplace's equation and its solutions for geometries of which this is a specific example is given in Journal of the Electrochemical Society 113 501 (1966). Two important features of the solutions from the point of view of this invention are that the variation in resistance between the extreme rotational positions increases as the disc radius becomes smaller and decreases as the distance $y$ becomes smaller. The magnitude of the ac component of the measured voltage thus increases as $r$ becomes smaller and as $y$ becomes greater.

This electrode configuration may be fabricated by inserting a small diameter gold wire into a hole near the end of a stainless steel rod, soldering a connection and allowing one end of the wire to project from the curved surface of the cylinder. The rod is then dipped in epoxy and cured. It is finally lathe turned to a cylinder and polished to the desired diameter. The finished cylinder is covered by an insulating epoxy coating 34, except for disc 28. The gold wire is typically 0.054 cm and the final cylinder diameter is 0.77 cm. The mentioned materials and dimensions are to be considered only as exemplary and other materials and dimensions can be used.

The configuration shown in FIG. 2B is a split-ring disc such as described in Journal of the Electrochemical Society 116 1117 (1969). Essentially, the electrode has two co-planar half-rings concentrically arranged around a disc. The axis of rotation is perpendicular to the plane of the disc. Due to the high degree of symmetry in this geometry, the variation in resistance is increased if only one of the half-rings is used as the active electrode.

The electrode may be fabricated from a stainless steel rod and tube adhesively bonded to each other. Epoxy is applied to the outside of the lower end of the tube and machined to give an epoxy insulating layer of about 0.1 cm thickness. The tube is then sawed both radially and axially along its length, as indicated, to expose the epoxy. For permanent insulation, the slots are filled with epoxy. The areas labeled A and B, forming two half-rings, are now electrically isolated from each other. An additional axial slot is cut near the top of one half-ring and an insulated wire inserted and adhesively bonded. This connects half-ring A to its brush area C. Similar brush contact areas made for the other half-ring and rod permit selection of any one of the electrodes as the active electrode. The gaps between the half-rings are less than 1 percent of the inner ring circumference. Other materials and dimensions can be used.

Figure 3:
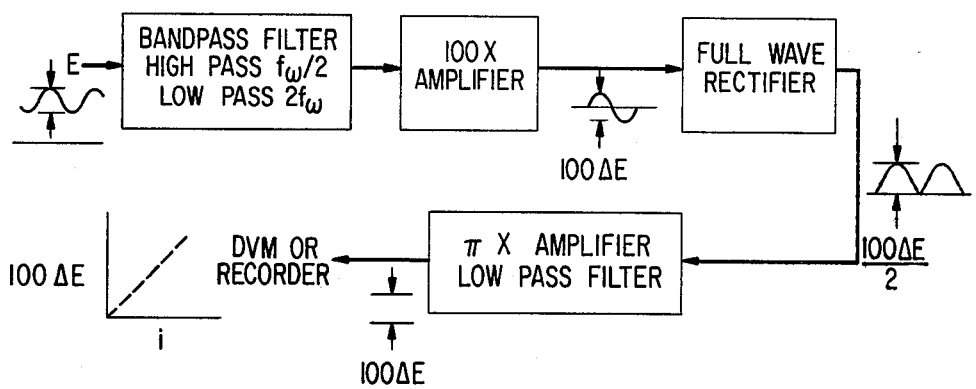
FIG. 3 is a schematic of a processing sequence for the voltage signal obtained between the rotating electrode and a cell electrode.

It is emphasized that the voltage between electrode 7 and rotating electrode 13 varies because of the varying dc solution resistance between electrode 7 and 13. The voltage measured has an ac component at the rotational angular velocity and the magnitude of the ac component, as explained below, permits determination of the solution conductivity and spatial current distribution. Both the motor speed control for the rotating electrode and the voltage signal processing are conventional and systems such as those described in Analytical Chemistry 46 2026 (1974) may be used. The voltage signal processing sequence is schematically illustrated in FIG. 3. The voltage signal goes through a bandpass filter which passes signals having a frequency near the rotational frequency, is amplified and passed through a full wave rectifier. The rectified signal is amplified and filtered to restore the average voltage to the peak-to-peak value and goes to either a voltmeter or recorder.

Two modes of operation are typical when solution conductivity is being determined. The current through the cell may be varied with time and both the current and the voltage recorded. Alternatively, current values may be digitally selected and the voltage read out on a digital voltmeter. When measuring the spatial current distribution, both current and voltage may be read out. A conventional galvanostat is used to control the current through the cell.

Figure 4:
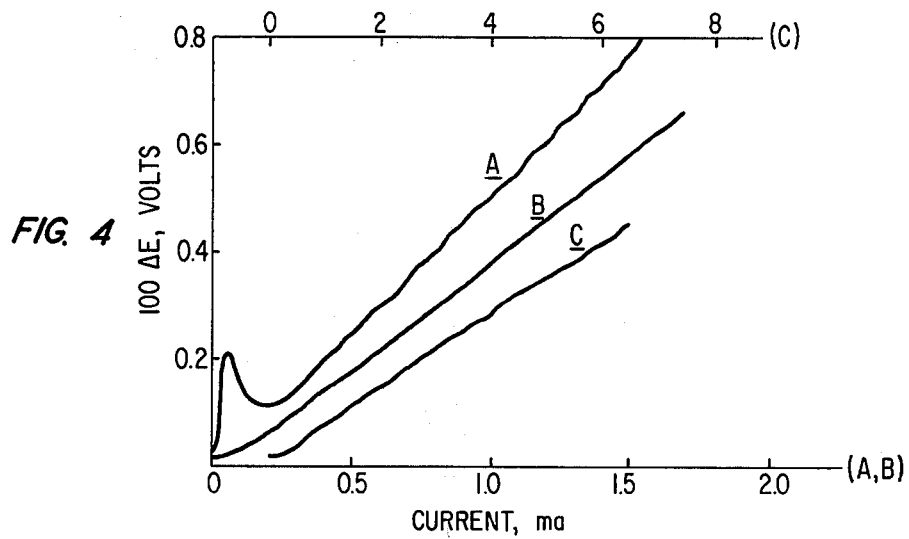
FIG. 4 is a graph showing the voltage versus cell current for several different rotating electrode and cell configurations.

FIG. 4 is a graph showing the processed voltage signals versus the scanned cell current for a 0.1M KCl solution. The solution temperature was 23.5 degrees C $\pm$ 0.5° C. The rotational frequency was 100 Hz and the bandpass filter passed frequencies between 50 Hz and 200 Hz. The curves show the recorded signals for three different geometries. A and B used a rotating disc electrode with the cell being operated in a two and three electrode mode, respectively; C used a split-ring disc electrode, with the cell operating in a three electrode mode. Although the plots were made with the rotating electrode operated cathodically, similar results were obtained when the current direction was reversed. The plotted voltage is the initially sensed voltage multiplied by 100.

Curve A has a spurious peak at low current levels. The spurious signal is believed due to mass transport limited current noise attributable to oxygen present in the KCl solution. The voltage signal yielding the peak is broadband noise found at a current level, 15 $\mu$amp at 100 Hz, that corresponds to the limiting current of oxygen reduction. This current level does not vary much with KCl concentration and the effect of the spurious signal on the voltage-current plots becomes smaller as the level of the constant current passed through the cell increases. The width of the peak, as viewed on the current axis, is determined by the current attributable to the mass transport limited reaction at the rotating electrode. In the limiting current region, the noise in the voltage is amplified and becomes large because the apparent electrode resistance is high. Beyond this region, the noise has a decreasing effect as the apparent electrode resistance becomes lower. The spurious peak disappears when the current passes in the opposite direction and oxygen reduction occurs at the larger and nonmoving electrode.

In some instances, depending upon the solution being measured and the constant current passing through the cell, this effect may constitute a drawback when a two electrode configuration is used. However, the effect is absent in the three electrode configurations (curves B and C) as no current passes through the rotating electrode in these cases and any current generated at the rotating electrode at the rotational frequency is negligible.

As it is apparent from the slopes of curves A and B in FIG. 4, the three electrode rotating disc configuration detects smaller values of $\Delta E/I$ than does the two electrode rotating disc configuration. The difference in sensitivity arises because the equipotential lines are more widely spaced in the three electrode configuration than they are in the two electrode configuration where the rotating electrode terminates current flow. However, with this decrease in sensitivity comes a decrease in the synchronous noise. In the two electrode configuration, there is some synchronous noise as variations in the disc surface condition due to passing current cause variations in the measured voltage that tend to be synchronized with the rotational frequency. This effect is not present in the three electrode configuration where the rotating electrode does not pass any current.

As shown by FIG. 4, the rotating split-ring disc configuration with one half ring used as the active electrode shows an approximately five fold reduction in sensitivity when compared with the rotating disc configuration. The lower sensitivity is attributed both to electrode geometry and to placement of the rotating electrode near the center of the solution volume. This placement and the described geometry yield only a small asymmetry for the rotating electrode when compared to the rotating disc electrode. The smaller asymmetry causes a correspondingly smaller variation in the solution resistance as the rotating electrode moves between its rotational extremes and leads to a smaller variation in magnitude of the ac component of the voltage when compared to the rotating disc electrode.

Although the variation in resistance due to the split-ring disc is less than the variation due to the rotating disc, the signal-to-noise ratios are approximately the same for both configurations. However, measurements made with the split-ring disc configuration begin to show curvature in the current-voltage plots at high current levels, i.e., the linearity of the current-voltage plots present at lower currents is lost. It is believed that this curvature or deviation from linearity is caused by the configuration geometry that causes disc products to be carried over the ring surface and alter the high current data because of changes in the effective composition of the solution. The configuration geometry reduces this effect in the rotating disc configurations.

The value of the dc voltage level may drift somewhat with time due to changing condition at the electrode surfaces. However, the magnitude of the ac component of the measured voltage should remain constant to the extent that the solution conductivity is not altered by the electrode reactions.

Curves, such as those in FIG. 4, permit the solution conductivity to be determined. The cell constant, $\theta$, equals $kR = \Lambda C \Delta E / 1,000 i$ where $k$ is the specific conductivity, R is the resistance, $\Lambda$ is the equivalent solution conductivity and C is the molar concentration. R may be measured with the cell containing any solution of known specific conductance and $\theta$ is computed for the particular apparatus. After $\theta$ is known, measurements of $\Delta E/i$ permit determination of the solution conductivity in units of $ohm^{-1} cm^3 molar equivalents^{-1}$.

If it is assumed that the solution is sensibly constant throughout the cell, in the three electrode configuration, the current at each point and thus, the spatial current distribution, may be determined by moving the rotating electrode to various positions within the cell. If this configuration is used in, e.g., a working electroplating bath, the current distributions may be accurately monitored on a real time basis and appropriate changes in the operating conditions can be made as needed.

Figure 5:
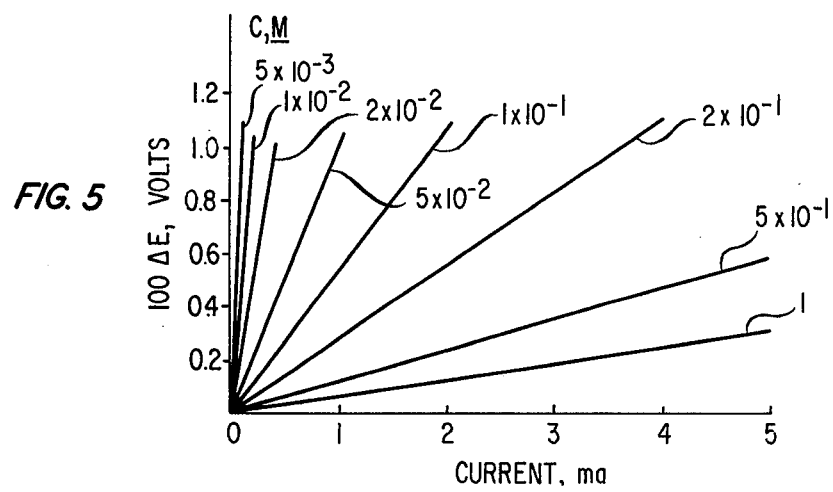
FIG. 5 is a graph showing the voltage versus cell current for different KCl concentrations.

FIG. 5 is a graph showing the voltage, again multiplied by 100, versus current plot for different KCl concentrations made with the two electrode rotating disc configuration. The concentrations vary from 0.005 M to 1 M and all of the curves are essentially linear over the entire plotted range. The large linear range of each curve and the wide variation in concentrations illustrate the range over which the invention may be employed.

If a single fixed speed for rotating the electrode is selected, the needed instrumentation is considerably simplified and the entire structure can be easily built into a portable unit for routine conductivity measurements. In the three electrode configuration, the rotating electrode can be used to map the spatial current distribution in operating electrochemical cells well outside the usual laboratory scale. The geometries described for the moving electrode illustrate how the sensitivity and spatial resolution of the apparatus may be varied.

What is claimed is:
1. Apparatus for measuring characteristics of a cell containing an electrolyte and having at least a first electrode comprising:
   an asymmetrically moving electrode;
   means for passing a constant current through said cell and through said first electrode;
   means for moving said asymmetrically moving electrode;
   means for measuring the voltage between said first electrode and said asymmetrically moving electrode;
   characterized in that said means for moving periodically varies the distance between said first electrode and said asymmetrically moving electrode thereby periodically varying the resistance and voltage between said first electrode and said asymmetrically moving electrode.

2. Apparatus as recited in claim 1 in which said asymmetrically moving electrode is a disc.

3. Apparatus as recited in claim 1 in which said asymmetrically moving electrode is a split ring.

4. Apparatus as recited in claim 1 in which said means for moving rotates said asymmetrically moving electrode in a plane about an axis of rotation.

5. Apparatus as recited in claim 4 in which said axis of rotation is perpendicular to said plane in which said asymmetrically moving electrode rotates.

6. Apparatus as recited in claim 5 in which said asymmetrically moving electrode is a disc.

7. Apparatus as recited in claim 5 in which said asymmetrically moving electrode is a split ring.

* * * * *